United States Patent [19] [11] 4,379,146
Greenlee et al. [45] Apr. 5, 1983

[54] SUBSTITUTED PHOSPHONAMIDES AS ANTIHYPERTENSIVES

[75] Inventors: William J. Greenlee, Teaneck; Elbert E. Harris; Arthur A. Patchett, both of Westfield; Eugene D. Thorsett, Fanwood, all of N.J.

[73] Assignee: Merck & Co., Inc., Rahway, N.J.

[21] Appl. No.: 318,221

[22] Filed: Nov. 5, 1981

Related U.S. Application Data

[63] Continuation-in-part of Ser. No. 235,336, Feb. 17, 1981.

[51] Int. Cl.³ .................. A61K 37/00; C07C 103/52; C07D 277/20

[52] U.S. Cl. .................. 424/177; 260/112.5 R; 260/943; 548/201; 548/341; 548/413; 548/414; 424/200; 424/211; 424/246; 424/274; 546/22; 548/112; 548/119

[58] Field of Search .............. 424/200, 177, 211, 246, 424/274; 260/112.5 R, 306.7 C, 326.2, 943, 326.13 R; 548/201, 341

[56] References Cited

U.S. PATENT DOCUMENTS 4,316,896 2/1982 Thorsett et al. .................. 424/200

Primary Examiner—Delbert R. Phillips
Attorney, Agent, or Firm—Salvatore C. Mitri

[57] ABSTRACT

There are disclosed substituted phosphonamides and related compounds which are useful as converting enzyme inhibitors and as antihypertensives.

24 Claims, No Drawings

SUBSTITUTED PHOSPHONAMIDES AS ANTIHYPERTENSIVES

BACKGROUND OF THE INVENTION

This is a continuation-in-part application of application Ser. No. 235,336 filed Feb. 17, 1981.

The invention in its broad aspects relates to substituted phosphonamides and related compounds which are useful as converting enzyme inhibitors and as antihypertensives. The compounds of this invention can be shown by the following formula

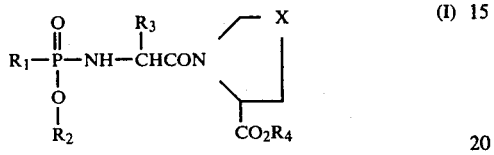

wherein $R_1$ is alkyl or substituted alkyl of $C_1$–$C_6$ wherein the substituent is halo, amino, acylamino; aralkyl wherein the alkyl is $C_1$–$C_4$ optionally substituted by amino or acylamino and wherein the aryl function is phenyl or naphthyl optionally substituted by halo or hydroxyl; or, heteroaralkyl wherein the alkyl is $C_1$–$C_4$ optionally substituted by amino or acylamino and wherein the heteroaryl group can be indolyl or thienyl;

$R_2$ is H, lower alkyl of $C_1$–$C_4$, aralkyl such as benzyl;

$R_3$ is lower alkyl of $C_1$–$C_6$ optionally substituted by an amino group;

$R_4$ is H, lower alkyl of $C_1$–$C_6$, aralkyl such as benzyl;

X is $(CH_2)_n$ wherein n is 1 or 2, CH—$OCH_3$, CH—OH, or S; and, the pharmaceutically acceptable salts thereof.

The lower alkyl groups represented by any of the variables include straight and branched chain hydrocarbon radicals such as for example, methyl, ethyl, propyl, isopropyl, butyl, isobutyl, t-butyl, pentyl, isopentyl, hexyl, and the like. The aralkyl groups represented by any of the above variables have from one to four carbon atoms in the alkyl portion thereof and include for example, benzyl, p-methoxy benzyl, and the like.

Aryl wherever it appears is represented by phenyl or naphthyl either or both of which can be substituted wherein the substituent is halo or hydroxyl.

Preferred are those compounds of Formula I wherein:

$R_1$ is alkyl or substituted alkyl of $C_1$–$C_6$ wherein the substituent is halo, amino, acylamino;

aralkyl wherein the alkyl is $C_1$–$C_4$ optionally substituted by amino or acylamino and the aryl function is a phenyl group; and, $R_3$ is lower alkyl of $C_1$–$C_6$.

Still more preferred compounds are those compounds of Formula I wherein X is S or $CH_2$.

Most preferred are those compounds of Formula I wherein:

$R_1$ is aralkyl wherein the alkyl is $C_1$–$C_4$ optionally substituted by amino or acylamino and the aryl function is a phenyl group;

$R_2$ and $R_4$ are both hydrogen;

$R_3$ is methyl; and,

X is $CH_2$.

The preferred, more preferred and most preferred compounds of Formula I also include the pharmaceutically acceptable salts thereof.

The products of Formula (I) and the preferred subgroups can be produced by one or more of the methods depicted in the following equations wherein $R_1$, $R_2$, $R_3$, $R_4$ and X are as defined above unless indicated otherwise:

METHOD I, ROUTE A

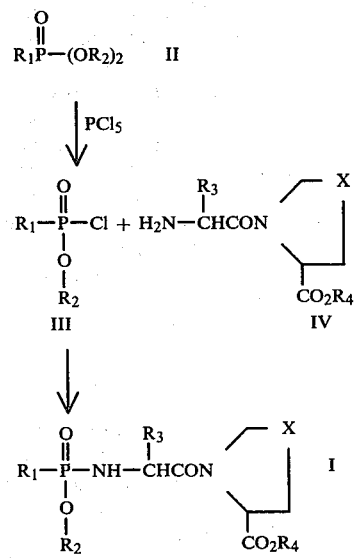

METHOD I, ROUTE B

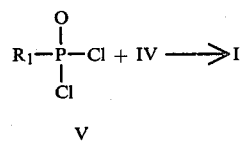

With reference to the foregoing equations, a phosphonic acid diester II ($R_2$=alkoxy, aralkoxy) which can be prepared by known methods, is converted to the monoester chloride III with $PCl_5$ in a suitable solvent, such as carbon tetrachloride [Houben-Weyl, *Methoden der Org. Chem.*, 12(1), 243 (1963)]. Reaction of this chloride with a dipeptide derivative IV, for example an ester where $R_4$=$OCH_2C_6H_5$, in the presence of a base such as triethylamine and in a suitable solvent like methylene chloride affords the desired product I.

If desired, I may be obtained where $R_2$=$R_4$=OH as, for example, from I where $R_2$=$R_4$=$OCH_2C_6H_5$ by catalytic hydrogenation using a catalyst such as palladium on carbon. Alternatively, a monoester may be obtained from a diester in a similar fashion when either $R_2$ or $R_4$=$OCH_2C_6H_5$. If desired, the mono or diesters may be converted to diacids by basic hydrolysis.

Alternatively, a phosphonyl dichloride V may be coupled to IV under aqueous base conditions to produce I where $R_2$=$R_4$=OH.

Products of general Formula I have two asymmetric carbons, namely, the carbon atoms to which $R_3$ and $CO_2R_4$ are attached. Optional substituents on the $R_1$ group may also produce a third asymmetric center. The compounds accordingly exist in diastereoisomeric forms or in racemic mixtures thereof, all of which are within the scope of the invention. Accordingly, the above described syntheses can utilize a diastereomer, the racemate, or one of the enantiomers as starting material. When diastereomers of IV are used in the synthetic procedure, the stereoisomers obtained in the product can be separated by conventional chromotographic or fractional crystallization methods. Preferably, the compounds of Formula I are obtained with the asymmetric carbon atoms in the S configuration. In general, the amino acid part-structures of Formula I are preferred in the L-configuration.

The compounds of this invention form basic salts with various inorganic and organic bases when either or both $R_2$ and $R_4$ are hydrogen and such salts are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salts, N-methyl-D-glucamine, salts with amino acids like arginine, lysine, and the like. Salts with organic and inorganic acids may also be prepared such as, for example, HCl, HBr, $H_2SO_4$, $H_3PO_4$, methanesulfonic, and the like. The non-toxic physiologically acceptable salts are preferred, although other salts are also useful, e.g., in isolating or purifying the product, as illustrated in the examples in the case of the disodium salt.

The salts may be formed by conventional means, as by reacting the free acid form of the product with one or more equivalents of the appropriate base or acid in a solvent or medium in which the salt is insoluble, or in water and removing the water in vacuo or by freeze drying, or by exchanging the ions of an existing salt for another ion on a suitable ion exchange resin.

The compounds of this invention inhibit angiotensin converting enzyme and thus block conversion of the decapeptide angiotensin I to angiotensin II. Angiotensin II is a potent pressor substance. Thus blood-pressure lowering results from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta,* 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.,* 104, 646 (1960) or in a high renin rat model such as that of S. Koletsky et al., *Proc. Soc. Exp. Biol. Med.,* 125, 96 (1967).

Thus, the compounds of this invention are useful as antihypertensives in treating hypertensive mammals, including humans and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage range of 100 to 1000 mg per patient optionally given several times, thus giving a total daily dose of from 100 to 4000 mg per day. The dose will vary depending on severity of disease, weight of patient and other factors which a person skilled in the art will recognize.

Also, the compounds of this invention may be given in combination with diuretics or other antihypertensives. Typically these are combinations whose individual per day dosages range from one-fifth of the minimally recommended clinical dosages to the maximum recommended levels for the entities when they are given singly. To illustrate these combinations, one of the antihypertensives of this invention effective clinically in the range 20–1000 milligrams per day can be effectively combined at levels ranging from 4–1000 milligrams per day with the following antihypertensives and diuretics in dose ranges per day as indicated:

hydrochlorothiazide (10–200 mg), timolol (5–60 mg), methyl dopa (65–2000 mg), the pivaloyloxyethyl ester of methyl dopa (30–1000 mg), indacrinone and variable ratios of its enantiomers (25–150 mg) and (+)-4-{3-{-[2-(1-hydroxycyclohexyl)-ethyl]-4-oxo-2-thiazolidinyl}-propyl}-benzoic acid (10–100 mg).

In addition, the triple drug combinations of hydrochlorothiazide (15–200 mg) plus amiloride (5–20 mg) plus converting enzyme inhibitor of this invention (4–1000 mg), or hydrochlorothiazide (15–200 mg) plus timolol (5–50 mg) plus the converting enzyme inhibitor of this invention (4–1000 mg) are effective combinations to control blood pressure in hypertensive patients.

The above dose ranges will be adjusted on a unit basis as necessary to permit divided daily dosage. Also, the dose will vary depending on the severity of the disease, weight of patient and other factors which a person skilled in the art will recognize.

Typically the compounds and combinations shown above are formulated into pharmaceutical compositions as discussed below.

About 100 to 1000 mg of a compound or of Formula I or a physiologically acceptable salt thereof or a mixture with diuretic and/or other antihypertensive compounds is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by column chromatography or fractional crystallization. Optical isomers are separated through the use of optically active acids or bases as resolving agents.

EXAMPLE 1

N-(3-Phenyl-1-propylphosphonyl)-(L)-alanyl-(L)-proline

Suspend 550 mg of sodium hydride in 30 ml dry DMF and add a solution of 5.25 g dibenzylphosphite in 20 ml DMF over 15 minutes. Stir the reaction at room temperature for one hour then add 4.0 g 1-phenyl-3-bromopropane in 5 ml DMF. After 20 hours at room temperature concentrate the reaction in vacuo and partition the residue between ether and $H_2O$. Wash the ether layer with water and brine, dry and concentrate in vacuo. Purify the crude diester by chromatography on silica gel eluting with 1:1 ethyl acetate:hexane.

Dissolve 1.9 g of this pure dibenzylester in 25 ml $CCl_4$ and add 1.05 g $PCl_5$. Heat the reaction under nitrogen at 58° for four hours. Concentrate the reaction in vacuo and store the residue for 24 hours under high vacuum. Isolate the monoester chloride as a thick yellow oil NMR ($CDCl_3$, TMS) $\delta 1.6$–$2.4$ (m, 4H); $\delta 2.5$–$2.9$ (m, 2H); $\delta 5.2$ (m, 2H); $\delta 7.0$–$7.5$ (m, 10H).

Add 1.5 g of this phosphonylchloride monoester and 1.7 g benzyl (L)-alanyl-(L)-prolinate hydrochloride to 20 ml $CH_2Cl_2$. Add a solution of 2.0 ml triethylamine in 20 ml $CH_2Cl_2$ over 30 minutes. After the addition is completed, stir the reaction at room temperature for 2 hours then concentrate in vacuo. Add ether to the residue, filter and concentrate the filtrate to a thick syrup. Purify the product by silica gel chromatography eluting with 95:5 ethyl acetate:acetonitrile. NMR ($CDCl_3$, TMS) $\delta 1.3$ (d, 3H); $\delta 1.9$–$2.3$ (m, 8H); $\delta 2.7$ (t, 2H); $\delta 3.3$–$4.7$ (m, 5H); $\delta 5.0$ (d of d, 2H); $\delta 5.2$ (s, 2H); $\delta 7.2$–$7.4$ (m+s, 15H). Mass spectrum: $M+=548$. m/e: 431 ($M+ -OCH_2C_6H_5$).

Dissolve 444 mg of this phosphonamide diester in 25 ml 1:1 $H_2O$:ethanol containing 136 mg $NaHCO_3$. Hydrogenate this mixture at 40 psig hydrogen pressure using 10% palladium on charcoal catalyst. Filter the reaction and concentrate the filtrate in vacuo. Dissolve the residue in $H_2O$ and freeze dry to isolate N-(3-phenyl-1-propylphosphonyl)-(L)-alanyl-(L)-proline as the disodium salt.

EXAMPLE 2

N-(2-Phenyl-1-ethylphosphonyl)-(L)-alanyl-(L)-proline

React 5.25 g dibenzylphosphite with 0.54 g sodium hydride and 3.7 g 2-phenethylbromide in DMF as described in Example 1. Chromatograph the crude product to isolate the pure diester. NMR ($CDCl_3$, TMS); $\delta 1.7$–$2.45$ (m, 2H); $\delta 2.5$–$3.2$ (m, 2H); $\delta 5.05$ (d, 4H, J=17 hz); $\delta 7.0$–$7.2$ (m+s, 15H).

React 1.55 g of this diester with 0.880 g $PCl_5$ in 20 ml $CCl_4$ as described in Example 1 to obtain the monoester chloride. NMR ($CDCl_3$, TMS) $\delta 2.2$–$3.4$ (m, 4H); $\delta 5.2$ (m, 2H); $\delta 7.2$–$7.5$ (m+s, 10H).

React 1.25 g of this monoester chloride with 1.6 g benzyl (L)-alanyl-(L)-prolinate hydrochloride as described in Example 1. Isolate, after silica gel chromatography, the desired diester. Mass Spectrum: $M+=534$, m/e: 427 ($M+ -OCH_2C_6H_5$); 426 (427—H)

Remove the benzyl groups as described in Example 1 and isolate N-(2-phenyl-1-ethylphosphonyl)-(L)-alanyl-(L)-proline disodium salt. NMR ($D_2O$), $\delta 1.45$ (d, 3H, J=7 hz); $\delta 1.7$–$2.4$ (m, 4H); $\delta 2.9$ (m, 2H) $\delta 3.4$–$4.5$ (m, 5H), $\delta 7.4$ (S, 5H); another signal obscured by $H_2O$ $\delta 4.8$.

EXAMPLE 3

N-Chloromethylphosphonyl-(L)-alanyl-(L)-alanine

Add 2.1 g methyl (L)-alanyl-(L)-alaninate hydrochloride to a solution of 2.0 g triethylamine in 100 ml $CH_2Cl_2$. Cool this solution to $-15°$ and add 1.67 g chloromethylphosphonyl dichloride in 50 ml $CH_2Cl_2$. Allow the reaction to reach room temperature and stir for one additional hour. Add the reaction mixture to 100 ml $H_2O$ keeping the pH at 6.5 by addition of 1 N NaOH. Separate the aqueous layer and freeze dry.

Dissolve the crude product in $H_2O$ and pass it through a Dowex 50 (Na+) column, eluting with $H_2O$. Combine the product containing fractions and freeze dry to obtain N-chloromethylphosphonyl-(L)-alanyl-(L)-alanine as the disodium salt.

EXAMPLE 4

N-[benzamidomethylphosphonyl]-(L)-alanyl-(L)-proline disodium salt

Add 3.0 g triethylamine to a slurry of 3.12 g (L)-alanyl-(L)-proline benzyl ester hydrochloride in 25 ml $CH_2Cl_2$. To this mixture add a solution of 2.87 g O-ethyl phthalimidomethylphosphonochloridate [M. Imoto, et. al., Bull. Chem. Soc. Japan, 45 2531 (1972)] in 25 ml THF and stir the mixture overnight. Dilute the reaction with 100 ml ethyl acetate and filter. Concentrate the filtrate, slurry the residue in THF, filter and concentrate. Purify the resulting oil by silica gel chromatography with ethyl acetate to obtain 2.95 g N-(ethyl phthalimidomethylphosphonyl)-(L)-alanyl-(L)-proline benzyl ester.

TLC on silica gel (EtAc, 3 developments) Rf=0.3 NMR ($CDCl_3$); $\delta 1.30$ (3H, t, J=7); $\delta 1.32$ (3H, d, J=7); $\delta 1.8$–$2.4$ (4H, m); $\delta 3.5$–$4.6$ (8H, m); $\delta 5.07$ (2H, 6s); $\delta 7.23$ (5H, s); $\delta 7.6$–$7.9$ (4H, m). MS m/e 527 ($M+$).

Analysis: Calculated for $C_{26}H_{30}N_3O_7P$: C, 59.20; H, 5.73; N, 7.97. Found: C, 58.76; H, 5.89; N, 7.86.

IR ($CHCl_3$): 2970, 1740, 1650, 1580, 1450 $cm^{-1}$.

To a solution of 0.595 g of this ester in 2 ml ethanol add a solution of 36 mg anhydrous hydrazine in 1 ml ethanol. Store the solution at room temperature for 72 hours then concentrate in vacuo. Slurry the residue with ethyl acetate, filter and concentrate the filtrate. Purify the crude product by silica gel chromatography using $CH_2Cl_2$:$CH_3OH$ (15:1) and isolate 0.27 g of N-(ethyl aminomethylphosphonyl)-(L)-alanyl-(L)-proline benzyl ester.

TLC (silica gel; 10:1 $CH_2Cl_2$:$CH_3OH$) Rf=0.3 NMR ($CDCl_3$); $\delta 1.1$–$1.5$ (6H, m); $\delta 1.9$–$2.3$ (4H, m); $\delta 2.7$–$3.1$ (2H, broad); $\delta 3.5$–$4.8$ (8H, m); $\delta 5.1$ (2H, m); $\delta 7.15$ (5H, m). IR(CHCl$_3$); 3400, 2980, 1740, 1650, cm$^{-1}$. MS: m/e 397 (M+).

Prepare a solution of 53 mg of this amine and 21 mg pyridine in 1.5 ml CH$_2$Cl$_2$. Cool the solution in an ice bath, add 33 mg benzoic anhydride in one portion, and stir the mixture vigorously for 15 minutes. Dilute the solution with 50 ml ethyl acetate and wash successively with 0.01 N HCl, saturated bicarbonate, H$_2$O, brine. Dry (MgSO$_4$) and concentrate to obtain N-(ethyl benzamidomethylphosphonyl)-(L)-alanyl-(L)-proline benzyl ester. Purify the product by silica gel chromatography using CH$_2$Cl$_2$:CH$_3$OH (10:1).

TLC on silica gel (10:1 CH$_2$Cl$_2$:CH$_3$OH) Rf=0.5. NMR (CDCl$_3$); δ1.2–1.5 (6H, m); δ1.8–2.2 (4H, m); δ3.3–4.5 (8H, m); δ5.1 (2H, m); δ7.3 (5H, s); δ7.4 (3H, m); δ7.6–7.9 (2H, m). IR (CHCl$_3$); 3400, 2980, 1740, 1660, 1570 cm$^{-1}$. MS m/e 501 (M+).

Hydrogenate a solution of 48 mg of this diester in 2 ml H$_2$O:dioxane (1:3) containing 16 mg sodium bicarbonate and 10 mg 10% Pd on carbon. Filter and concentrate the filtrate to obtain N-(benzamidomethylphosphonyl)-(L)-alanyl-(L)-proline disodium salt.

EXAMPLE 5

N-(aminomethylphosphonyl)-(L)-alanyl-(L)-proline

Hydrogenate 962 mg N-(ethyl phthalimidomethylphosphonyl)-(L)-alanyl-(L)-proline benzyl ester (prepared in Example 4) in 10 ml ethanol using 150 mg 10% Pd on charcoal. Filter and concentrate the filtrate to obtain 736 mg of N-(ethyl phthalimidomethylphosphonyl)-(L)-alanyl-(L)-proline.

TLC on silica gel (20:5:1:1 EtAc; pyr:HOAc:H$_2$O), Rf=0.4. NMR (CDCl$_3$) δ1.0–1.5 (6H, m); δ1.8–2.3 (4H, m); δ3.65 (2H, q, J=7); δ3.9–4.5 (8H, m); δ7.6–7.9 (5H, s); δ8.0–8.2 (1H, broad).

To an ice cold solution of 736 mg of this imide and 182 mg triethylamine in 5 ml CH$_2$Cl$_2$ add dropwise a solution of 58 mg hydrazine in 5 ml CH$_2$Cl$_2$. Continue stirring overnight at room temperature, filter and concentrate the filtrate. Chromatograph the residue on Dowex 50 (H+) and elute with aqueous pyridine to obtain N-(ethyl aminomethylphosphonyl)-(L)-alanyl-(L)-proline.

TLC (1:1:1:1 n-BuOH: HOAc:H$_2$O:EtAc) Rf=0.5. NMR (CD$_3$OD): δ1.33, δ1.37 (3H, pair of t, J=7); δ1.3–1.6 (3H, m); δ1.8–2.5 (4H, m); δ3.2–3.8 (4H, m); δ3.9–4.5 (4H, m). MS m/e 523 (M+, tristrimethylsilyl).

Stir a solution of 50 mg of this phosphonamide and 27 mg sodium bicarbonate in 0.7 ml H$_2$O for 18 hours. Chromatograph the reaction over Dowex 50 (H+) eluting with aqueous pyridine to obtain, after freeze drying, N-(aminomethylphosphonyl)-(L)-alanyl-(L)-proline.

TLC (silica gel; 1:1:1:1 n.BUOH:HOAc:H$_2$O:EtAc), Rf=0.45. NMR (CD$_3$OD); δ1.43, δ1.53, (3H, pair of d, J=7); δ1.7–2.4 (4H, m); δ3.4–4.4 (6H, m); MS m/e 495 (M+, tristrimethylsilyl).

EXAMPLE 6

N-(1-benzamido-2-phenyl-1-ethylphosphonyl)-(L)-alanyl-(L)-proline

To 45.8 g benzylamine in 50 ml CH$_2$Cl$_2$ add rapidly 51.3 g freshly distilled phenylacetaldehyde in 30 ml CH$_2$Cl$_2$. Add 40 g Na$_2$SO$_4$ and stir for 45 minutes. Filter, concentrate the filtrate, combine the residue with 56 g diethylphosphite and heat the mixture at 140° for 2 hours. Chromatograph the crude product over silica gel eluting with hexane:ethyl acetate (2:1) to obtain 31 g diethyl 1-benzylamino-2-phenyl-1-ethylphosphonate.

TLC on silica gel (1:1 hexanes —EtAc), Rf=0.5. NMR (CDCl$_3$); δ1.32 (3H, t, J=7); δ1.33 (3H, t, J=7); δ1.7 (1H, s); δ3.00 (2H, ABX, AB=21, JAB=4, JAX=JBX=10); δ3.80 (2H, s); δ4.0–4.5 (5H, m); δ7.0–7.4 (10H, m). MS m/e 347 (M+).

Convert 12.9 of this amine to its hydrochloride salt with HCl in ether. mp. 129°–130° (from THF-ether).

Hydrogenate 5.00 g of this amine hydrochloride in 25 ml ethanol using 0.5 g 10% Pd on carbon. Filter and concentrate the filtrate to obtain diethyl 1-amino-2-phenyl-1-ethylphosphonate hydrochloride.

TLC on silica gel (20:5:1:1 EtAc:pyr:HOAc:H$_2$O) Rf=0.5 NMR (CDCl$_3$); δ1.08 (3H, t, J=7); δ1.42 (3H, t, J=7); δ3.1–3.8 (2H, m); δ3.9–4.5 (5H, m); δ7.2–7.6 (5H, m); δ8.6–9.4 (3H, broad). TLC on silica gel (20:5:1:1 EtAc:pyr:HOAc:H$_2$O) Rf=0.5.

Reflux a mixture of 663 mg of this amino ester hydrochloride, 385 mg phthalic anhydride and 443 mg triethylamine in 15 ml toluene for three hours. Cool, filter and concentrate the reaction mixture.

Purify the residue by silica gel chromatography eluting with hexane-ethyl acetate (1:1) to obtain pure diethyl 1-phthalimido-2-phenyl-1-ethylphosphonate.

TLC (silica gel; EtAc) Rf=0.45. NMR (CDCl$_3$): δ1.30 (3H, t, J=7); δ1.33 (3H, t, J=7); δ3.3–4.0 (2H, m); δ4.62 (4H, pentet of d, J=9,3); δ4.98 (1H, ddd, J=5, 11, 18); δ7.17 (5H, s); δ7.67 (4H, m). MS m/e 387 (M+). IR (CHCl$_3$); 3000, 1775, 1730 cm$^{-1}$.

Reflux, with efficient stirring, 866 mg of the phthalimido derivative and 499 mg phosphorus pentachloride in 4 ml benzene for 16 hours. Remove the solvent in vacuo to obtain ethyl 1-phthalimido-2-phenyl-1-ethylphosphonochloridate.

Dissolve this crude chloro ester in 5 ml THF and add dropwise over 10 minutes to 700 mg of (L)-alanyl-(L)-proline benzyl ester and 0.94 ml triethylamine in 6 ml methylene chloride. After stirring for 20 hours, filter and concentrate the reaction. Chromatograph the residue on silica gel with ethyl acetate to obtain pure N-(ethyl 1-phthalimido-2-phenyl-1-ethylphosphonyl)-(L)-alanyl-(L)-proline benzyl ester.

TLC on silica gel (EtAc) Rf=0.2.

Analysis: Calculated for C$_{33}$H$_{36}$N$_3$O$_4$P: C, 64.17; H, 5.88; N, 6.80; Found: C, 63.77; H, 6.18; N, 6.21. MS m/e 617 (M+). NMR (CDCl$_3$); δ1.0–1.6 (6H, m); δ1.9–2.3 (4H, m); δ3.2–4.6 (9H, m); δ5.12 (2H, s); δ7.12 (5H, s); δ7.32 (5H, s); δ7.6–7.8 (4H, m). IR (CHCl$_3$) 3000, 1775, 1740 (shoulder), 1730, 1650 cm$^{-1}$.

Convert this compound to N-(ethyl 1-phthalimidyl-2-phenyl-1-ethylphosphonyl)-(L)-alanyl-(L)-proline as described in Example 5.

TLC (silica gel, ethyl acetate:pyridine: acetic acid:water; 20:5:1:1) Rf=0.2. NMR (CDCl$_3$) δ1.3–1.6 (3H, m); δ1.9–2.4 (4H, m); δ3.3–4.0 (7H, m); δ4.0–4.9 (3H, m); δ7.1 (5H, s); δ7.7 (4H, m).

As described in Example 5, convert this imide to N-(ethyl 1-amino-2-phenyl-1-ethylphosphonyl)-(L)-alanyl-(L)-proline.

TLC (silica gel 1:1:1:1 BuOH, H$_2$O, EtAc; AcOH) Rf=0.55. NMR (DMSO-d$_6$); δ1.34 (3H, d, J=4); δ1.8–2.3 (4H, m); δ2.7–2.9 (2H, m); δ3.0–3.2 (2H, m); δ5.54 (3H, d, J=14), δ5.58 (3H, d, J=14); δ3.5–3.9 (1H, m); δ4.1–4.3 (2H, m); δ7.1–7.5 (5H, m).

To an ice cold solution of 0.160 g of the above amine and 61.8 mg sodium bicarbonate in 2 ml H$_2$O add with vigorous stirring 0.062 g benzoyl chloride. Stir the mixture at room temperature overnight. Treat the reaction mixture with 5 g Dowex 50 (H+) and 2 ml methanol and filter. Freeze dry the filtrate and purify the residue on LH-20 (CH$_3$OH) to obtain N-(1-benzamido-2-phenyl-1-ethylphosphonyl)-(L)-alanyl-(L)-proline.

TLC (silica gel; 3:1:1:1 EtAc:BuOH:H$_2$O:AcOH) Rf=0.50. NMR (CDCl$_3$); δ1.35 (3H, d, J=3); δ1.9-2.3 (4H, m); δ2.8-3.4 (2H, m); δ3.5-3.8 (4H, m); δ4.44 (1H, m); δ4.78 (1H, m); δ4.94 (1H, t, J=2); δ7.0-8.0 (10H, m).

EXAMPLE 7

N-(1-amino-2-phenyl-1-ethylphosphonyl)-(L)-alanyl-(L)-proline

Add over 30 minutes 4.23 g benzylchloroformate to a mixture of 6.3 g sodium bicarbonate and 5.0 g 1-amino-2-phenyl-1-ethylphosphonic acid [prepared by the method of J. Oleksyszyn, et. al., Synthesis, 479 (1978)] in 50 ml H$_2$O and 20 ml THF and continue stirring for 2 hours. Acidify the reaction with 6 N HCl and extract with ether. Dry the ether extacts, filter, and concentrate. Redissolve the residue in ether and treat the solution with ethereal diazomethane to obtain dimethyl 1-Cbz-amino-2-phenyl-1-ethylphosphonate.

TLC (silica gel; 10:1 CH$_2$Cl$_2$:CH$_3$OH) Rf=0.55. NMR (CDCl$_3$); δ2.7-3.4 (2H, m), δ3.70 (3H, d, J=11); δ3.71 (3H, d, J=11); δ4.1-4.8 (1H, m); δ5.00 (2H, s); δ5.7 (1H, broad, d, J=9); δ7.2 (10H, s). MS: m/e 363 (M+).

Hydrogenate this diester in benzene using 10% palladium on carbon and obtain dimethyl 1-amino-2-phenyl-1-ethylphosphonate.

Reflux 2.6 g of this amine, 1.68 g phthalic anhydride, and 1.1 ml triethylamine in 40 ml toluene for 2 hours while removing water with a Dean-Stark trap. Cool, filter, and concentrate the reaction then chromatograph the residue on silica gel with hexane-ethyl acetate to obtain dimethyl 1-phthalimidyl-2-phenyl-1-ethyl phosphonate.

Mp 91°-93°. Anal. Calc. for C$_{18}$H$_{18}$NO$_5$P: C, 60.17; H, 5.05; N, 3.90. Found: C, 60.69; H, 5.10; N, 3.90. TLC (silica gel, EtAc) Rf=0.5. NMR (CDCl$_3$) δ3.2-4.0 (2H, m), δ3.78 (3H, d, J=10); δ3.82 (3H, d, J=10); δ5.00 (1H, ddd, J=19, 12, 5); δ7.13 (5H, s); δ7.68 (4H, m).

Heat a mixture of 1.08 g of this imide and 0.687 g phosphorous pentachloride in 7.5 ml benzene at 60° for 8 hours. Concentrate the reaction in vacuo to an oil.

Dissolve this chlorophosphonate in 5 ml CH$_2$Cl$_2$ and add to an ice cold mixture of 0.94 g (L)-alanyl-(L)-proline benzyl ester hydrochloride and 1.25 ml triethylamine in 5 ml CH$_2$Cl$_2$ and stir for 18 hours. Filter and concentrate the reaction mixture, slurry the residue in THF, filter and concentrate the filtrate. Chromatograph the residue on silica gel with ethyl acetate to obtain N-(methyl 1-phthalimidyl-2-phenyl-1-ethylphosphonyl)-(L)-alanyl-(L)-proline benzyl ester.

TLC (silica gel 10:1 CH$_2$Cl$_2$:CH$_3$OH) Rf=0.65 (3 overlapping spots). NMR (CDCl$_3$); δ1.3-1.6 (3H, m); δ1.8-2.4 (4H, m); δ3.4-4.0 (7H, m); δ4.2-5.3 (3H, m); δ5.1 (2H, broad s); δ7.1 (5H, s); δ7.4 (5H, s); δ7.7 (4H, broad s). MS: m/e 603 (M+).

Convert this compound to N-(1-amino-2-phenyl-1-ethyl-phosphonyl)-(L)-alanyl-(L)-proline as described in Example 5.

EXAMPLE 8

N-(Benzylphosphonyl-(L)-alanyl-(L)-proline

React 5.25 g dibenzylphosphite with 0.54 g sodium hydride and 2.55 g benzyl chloride in DMF as described in Example 1. Purify the crude product by chromatography to isolate the pure diester. NMR (CDCl$_3$, TMS): δ3.1 (d, J=22 hz, 2H); δ4.9 (d, J=9 hz, 4H); δ7.2 (m, 15H).

Convert this diester to the monoester chloride as described in Example 1. React this acid chloride with (L)-alanyl-(L)-proline benzyl ester hydrochloride as described in Example 1 and isolate, after chromatography, the desired diester. Anal. Calc. (C$_{29}$H$_{33}$N$_2$O$_5$P): C, 66.91; H, 6.39; N, 5.38. Found: C, 66.61; H, 6.47; N, 5.25.

Remove the benzyl groups as described in Example 1 and isolate N-(benzylphosphonyl)-(L)-alanyl-(L)-proline disodium salt.

NMR (D$_2$O; dioxane=3.75): δ1.1 (d, 3H, J=6 hz); δ1.7-2.3 (m, 4H); δ2.9 (d, 2H, J=20 hz); δ3.2-4.8 (m, 4H); δ7.15 (s, 5H).

What is claimed:

1. A compound of the general formula

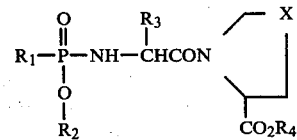

wherein:
R$_1$ is alkyl or substituted alkyl of C$_1$-C$_6$ wherein the substituent is halo, amino, acylamino;
  aralkyl wherein the alkyl is C$_1$-C$_4$ optionally substituted by amino or acylamino and wherein the aryl function is phenyl or naphthyl optionally substituted by halo or hydroxyl; or,
  heteroaralkyl wherein the alkyl is C$_1$-C$_4$ optionally substituted by amino or acylamino and wherein the heteroaryl group can be indolyl or thienyl;
R$_2$ is H, lower alkyl of C$_1$-C$_4$, aralkyl;
R$_3$ is lower alkyl of C$_1$-C$_6$ optionally substituted by an amino group;
R$_4$ is H, lower alkyl of C$_1$-C$_6$, aralkyl;
X is (CH$_2$)$_n$ wherein n is 1 or 2; and,
the pharmaceutically acceptable salts thereof.

2. A compound of claim 1 wherein:
R$_1$ is alkyl or substituted alkyl of C$_1$-C$_6$ wherein the substituent is halo, amino, acylamino;
  aralkyl wherein the alkyl is C$_1$-C$_4$ optionally substituted by amino or acylamino and the aryl function is a phenyl group; and,
R$_3$ is lower alkyl of C$_1$-C$_6$.

3. A compound of claim 2 wherein
R$_1$ is aralkyl wherein the alkyl is C$_1$-C$_4$ optionally substituted by amino or acylamino and the aryl function is a phenyl group;
R$_2$ and R$_4$ are both hydrogen;
R$_3$ is methyl; and,
X is CH$_2$.

4. Compounds of claim 1 wherein the asymmetric carbons are in the L configuration.

5. The compound: N-(2-phenyl-1-ethylphosphonyl)-L-alanyl-L-proline.

6. The compound: N-(3-phenyl-1-propylphosphonyl)-L-alanyl-L-proline.

7. A pharmaceutical composition useful in the treatment of hypertension which comprises a pharmaceutically acceptable carrier and an antihypertensivity effective amount of a compound of the formula:

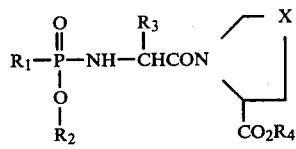

wherein:
$R_1$ is alkyl or substituted alkyl of $C_1$–$C_6$ wherein the substituent is halo, amino, acylamino;
 aralkyl wherein the alkyl is $C_1$–$C_4$ optionally substituted by amino or acylamino and wherein the aryl function is phenyl or naphthyl optionally substituted by halo or hydroxyl; or,
 heteroaralkyl wherein the alkyl is $C_1$–$C_4$ optionally substituted by amino or acylamino and wherein the heteroaralkyl group can be indolyl or thienyl;
$R_2$ is H, lower alkyl of $C_1$–$C_4$, aralkyl;
$R_3$ is lower alkyl of $C_1$–$C_6$ optionally substituted by an amino group;
$R_4$ is H, lower alkyl of $C_1$–$C_6$, aralkyl;
X is $(CH_2)_n$ wherein n is 1 or 2; and,
the pharmaceutically acceptable salts thereof.

8. The composition of claim 7 wherein:
$R_1$ is alkyl or substituted alkyl of $C_1$–$C_6$ wherein the substituent is halo, amino, acylamino;
 aralkyl wherein the alkyl is $C_1$–$C_4$ optionally substituted by amino or acylamino and the aryl function is a phenyl group; and,
$R_3$ is lower alkyl of $C_1$–$C_6$.

9. The composition of claim 8 wherein:
$R_1$ is aralkyl wherein the alkyl is $C_1$–$C_4$ optionally substituted by amino or acylamino and the aryl function is a phenyl group;
$R_2$ and $R_4$ are both hydrogen;
$R_3$ is methyl; and,
X is $CH_2$.

10. The composition of claim 7 wherein the asymmetric carbon atoms in said compound are in the L configuration.

11. The composition of claim 7 wherein said compound is N-(2-phenyl-1-ethylphosphonyl)-L-alanyl-L-proline.

12. The composition of claim 7 wherein said compound is N-(3-phenyl-1-propylphosphonyl)-L-alanyl-L-proline.

13. A pharmaceutical composition useful in the treatment of hypertension which comprises a pharmaceutically acceptable carrier and an antihypertensively effective amount of a compound of the formula:

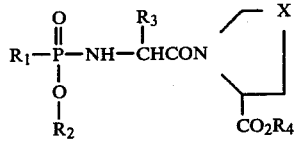

wherein:
$R_1$ is alkyl or substituted alkyl of $C_1$–$C_6$, wherein the substituent is halo, amino, acylamino;
 aralkyl wherein the alkyl is $C_1$–$C_4$ optionally substituted by amino or acylamino and wherein the aryl function is phenyl or naphthyl optionally substituted by halo or hydroxyl; or,
 heteroaralkyl wherein the alkyl is $C_1$–$C_4$ optionally substituted by amino or acylamino and wherein the heteroaralkyl group can be indolyl or thienyl;
$R_2$ is H, lower alkyl of $C_1$–$C_4$, aralkyl;
$R_3$ is lower alkyl of $C_1$–$C_6$ optionally substituted by an amino group;
$R_4$ is H, lower alkyl of $C_1$–$C_6$, aralkyl;
X is $(CH_2)_n$ wherein n is 1 or 2;
the pharmaceutically acceptable salts thereof; and, a diuretic and/or other antihypertensive compound selected from the group: hydrochlorothiazide, timolol, methyldopa, the pivaloyloxyethyl ester of methyldopa, indacronine and variable ratios of its enantiomers, (+)-4-{3-{[2-(1-hydroxycyclohexyl)-ethyl]-4-oxo-thiazolidinyl}propyl}-benzoic acid as well as combinations and mixtures thereof.

14. The composition of claim 13 wherein:
$R_1$ is alkyl or substituted alkyl of $C_1$–$C_6$ wherein the substituent is halo, amino, acylamino;
 aralkyl wherein the alkyl is $C_1$–$C_4$ optionally substituted by amino or acylamino and the aryl function is a phenyl group; and
$R_3$ is lower alkyl of $C_1$–$C_6$.

15. The composition of claim 14 wherein:
$R_1$ is aralkyl wherein the alkyl is $C_1$–$C_4$ optionally substituted by amino or acylamino and the aryl function is a phenyl group;
$R_2$ and $R_4$ are both hydrogen;
$R_3$ is methyl; and,
X is $CH_2$.

16. The composition of claim 13 wherein the asymmetric carbon atoms in said compound are in the L configuration.

17. The composition of claim 13 wherein said compound is N-(2-phenyl-1-ethylphosphonyl)-L-alanyl-L-proline.

18. The composition of claim 13 wherein said compound is N-(3-phenyl-1-propylphosphonyl)-L-alanyl-L-proline.

19. A method for treating hypertension which comprises administering to a patient in need of such treatment an antihypertensively effective amount of a compound having the formula:

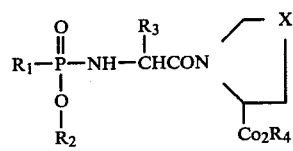

wherein:
$R_1$ is alkyl or substituted alkyl of $C_1$–$C_6$ wherein the substituent is halo, amino, acylamino;
 aralkyl wherein the alkyl is $C_1$–$C_4$ optionally substituted by amino or acylamino and wherein the aryl function is phenyl or naphthyl optionally substituted by halo or hydroxyl; or,
 heteroaralkyl wherein the alkyl is $C_1$–$C_4$ optionally substituted by amino or acylamino and wherein the heteroaralkyl group can be indolyl or thienyl;
$R_2$ is H, lower alkyl of $C_1$–$C_4$, aralkyl;

$R_3$ is lower alkyl of $C_1$–$C_6$ optionally substituted by an amino group;
$R_4$ is H, lower alkyl of $C_1$–$C_6$, aralkyl;
X is $(CH_2)_n$ wherein n is 1 or 2; and,
the pharmaceutically acceptable salts thereof.

20. The method of claim 19 wherein:
$R_1$ is alkyl or substituted alkyl of $C_1$–$C_6$ wherein the substituent is halo, amino, acylamino;
aralkyl wherein the alkyl is $C_1$–$C_4$ optionally substituted by amino or acylamino and the aryl function is a phenyl group; and,
$R_3$ is lower alkyl of $C_1$–$C_6$.

21. The method of claim 20 wherein:
$R_1$ is aralkyl wherein the alkyl is $C_1$–$C_4$ optionally substituted by amino or acylamino and the aryl function is a phenyl group;
$R_2$ and $R_4$ are both hydrogen;
$R_3$ is methyl; and,
X is $CH_2$.

22. The method of claim 19 wherein the asymmetric carbon atoms in said compound are in the L configuration.

23. The method of claim 19 wherein said compound is N-(2-phenyl-1-ethylphosphonyl)-L-alanyl-L-proline.

24. The method of claim 19 wherein said compound is N-(3-phenyl-1-propylphosphonyl)-L-alanyl-L-proline.

* * * * *